(12) United States Patent
Andrus et al.

(10) Patent No.: US 9,647,386 B2
(45) Date of Patent: May 9, 2017

(54) PERCUTANEOUS CONNECTOR AND ASSOCIATED METHODS OF USE

(71) Applicant: HeartWare, Inc., Miami Lakes, FL (US)

(72) Inventors: Lance Lynn Andrus, Southborough, MA (US); Andre Castillo, Aventura, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 14/738,443

(22) Filed: Jun. 12, 2015

(65) Prior Publication Data
US 2015/0364863 A1    Dec. 17, 2015

Related U.S. Application Data

(60) Provisional application No. 62/097,304, filed on Dec. 29, 2014, provisional application No. 62/011,290, filed on Jun. 12, 2014.

(51) Int. Cl.
*H01R 13/62* (2006.01)
*A61M 1/12* (2006.01)
(Continued)

(52) U.S. Cl.
CPC ....... *H01R 13/6205* (2013.01); *A61M 1/1008* (2014.02); *A61M 1/127* (2013.01);
(Continued)

(58) Field of Classification Search
CPC ........... H01R 13/6205; H01R 13/5224; A61M 2039/0261
(Continued)

(56) References Cited

U.S. PATENT DOCUMENTS

| 3,663,965 A | 5/1972 | Lee, Jr. et al. |
| 3,786,391 A * | 1/1974 | Mathauser ......... H01R 13/6205 335/205 |

(Continued)

FOREIGN PATENT DOCUMENTS

| WO | 0183023 A2 | 11/2001 |
| WO | 2008106717 A1 | 9/2008 |

(Continued)

OTHER PUBLICATIONS

International Search Report Application No. PCT/US2015/035657 dated Aug. 24, 2015.

*Primary Examiner* — Ross Gushi
(74) *Attorney, Agent, or Firm* — Christopher & Weisberg, P.A.

(57) ABSTRACT

In one embodiment, the present invention includes a percutaneous skin connector including a base and a cap. The base has a channel extending through it and a plurality of base magnets are positioned around the channel and exposed at a base surface. A skirt which allows tissue ingrowth extends from the base to further secure the base to the patient. The connector also includes a cap with a bore extending through it and a plurality of cap magnets positioned around the bore and exposed at a cap surface. The base magnets and cap magnets attract and align the cap surface to the base surface. The connector further includes a release mechanism adapted to at least partially separate the cap from the base when the cap is rotated relative to the base and out of alignment with the base.

25 Claims, 5 Drawing Sheets

(51) Int. Cl.
    *A61M 39/02*     (2006.01)
    *A61M 1/10*     (2006.01)
    *H01R 13/52*     (2006.01)
    *H01R 13/24*     (2006.01)

(52) U.S. Cl.
    CPC . *A61M 39/0247* (2013.01); *A61M 2039/0267* (2013.01); *A61M 2039/0288* (2013.01); *A61M 2205/3507* (2013.01); *A61M 2205/3515* (2013.01); *H01R 13/2421* (2013.01); *H01R 13/5224* (2013.01)

(58) Field of Classification Search
    USPC .......................................................... 439/39
    See application file for complete search history.

(56) References Cited

U.S. PATENT DOCUMENTS

| | | |
|---|---|---|
| 4,004,298 A | 1/1977 | Freed |
| 4,025,964 A | 5/1977 | Owens |
| 5,507,303 A | 4/1996 | Kuzma |
| 5,715,837 A | 2/1998 | Chen |
| 5,782,645 A | 7/1998 | Stobie et al. |
| 6,688,861 B2 | 2/2004 | Wampler |
| 6,761,681 B2 | 7/2004 | Schmid et al. |
| 7,780,639 B2 | 8/2010 | Van Lue |
| 7,793,987 B1 | 9/2010 | Busch et al. |
| 7,856,986 B2 | 12/2010 | Darley |
| 8,066,628 B1 | 11/2011 | Jeevanandam et al. |
| 8,323,174 B2 | 12/2012 | Jeevanandam et al. |
| 8,326,421 B2 | 12/2012 | Jeevanandam et al. |
| 8,545,255 B2 | 10/2013 | Litzler et al. |
| 8,608,637 B2 | 12/2013 | Jeevanandam et al. |
| 8,628,460 B2 | 1/2014 | Yomtov et al. |
| 8,684,905 B2 | 4/2014 | Jeevanandam et al. |
| 8,974,422 B2 * | 3/2015 | Gill ................... A61M 39/0247 604/175 |
| 2007/0060891 A1 * | 3/2007 | Skiera ................... A61F 2/2814 604/175 |
| 2009/0293238 A1 | 12/2009 | Davis |
| 2011/0160516 A1 | 6/2011 | Dague et al. |
| 2011/0298304 A1 | 12/2011 | Cotter |
| 2012/0178270 A1 * | 7/2012 | McElroy ................ H01R 13/22 439/39 |
| 2014/0273545 A1 * | 9/2014 | Shah ................. A61M 39/0247 439/39 |

FOREIGN PATENT DOCUMENTS

| | | |
|---|---|---|
| WO | 2009029977 A1 | 3/2009 |
| WO | 2013188400 A1 | 12/2013 |

* cited by examiner

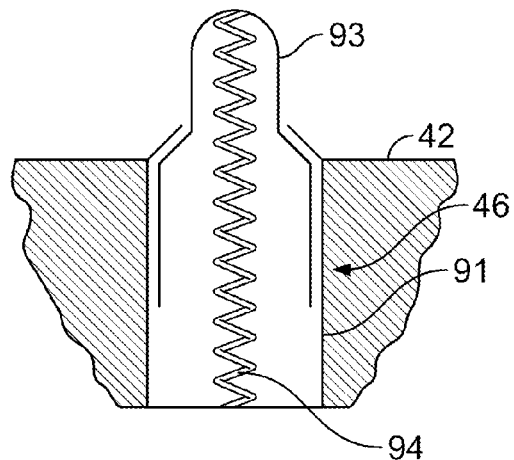
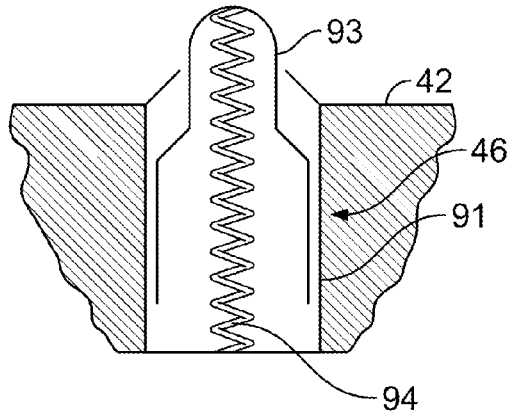
FIG. 9A    FIG. 9B
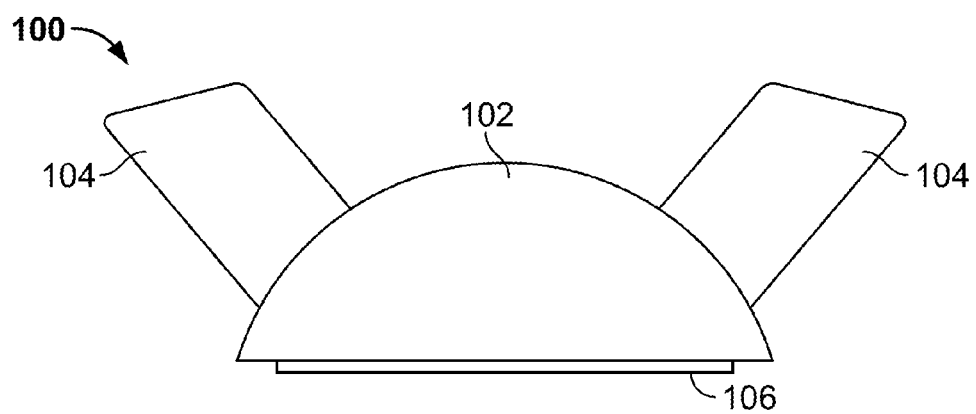
FIG. 10

PERCUTANEOUS CONNECTOR AND ASSOCIATED METHODS OF USE

CROSS-REFERENCE TO RELATED APPLICATIONS

This application claims the benefit of the filing date of U.S. Patent Application No. 62/011,290, filed Jun. 12, 2014, and U.S. Patent Application No. 62/097,304 filed Dec. 29, 2014, the disclosures of which are hereby incorporated herein by reference.

BACKGROUND OF THE INVENTION

The present invention relates to an improved device and method for connecting a device implanted inside the body of a patient to an external controller.

Thousands of heart patients who suffer from severe ventricular heart failure could benefit from cardiac transplantation. However, because of a shortage of donor hearts, most of these patients have a shortened life span characterized by frequent hospitalizations, severe physical disability, and death from congestive failure or cardiogenic shock, and do not survive long enough for a donor heart to become available.

One medical device developed to aid these heart patients is a heart pump such as a ventricular assist device ("VAD") which enables heart patients to return to prolonged and productive lives. Heart pumps are typically implanted in the patient and are connected to the left ventricle of the heart. One end of a tube such as a graft is connected to the heart pump and the other end is connected to the ascending aorta or the descending aorta. Once connected, the heart pump pumps blood from the left ventricle to the ascending or descending aorta to improve blood flow.

Most VADs utilize an external controller and power source. An electrical connection must therefore be established across the boundary of a patient's skin between the internal pump and external controller. A typical way to provide this connection is through the use of a percutaneous connector which provides an access way into the patient's body to establish the connection.

Traditional percutaneous connectors include an internal portion and an external portion. The internal portion is implanted into the body and extends through the patient's skin. The external portion attaches to the internal portion to establish the electrical connection. The connection between the two portions must be strong enough to maintain the connection during normal use, but not so strong as to cause patient discomfort when disconnecting the portions. A detachable connector must also be properly aligned to ensure the correct electrical connection is established.

Accordingly, there is a need for an improved connector which securely establishes an electrical connection between an internal device and external controller and which provides a detachable connection which minimizes patient discomfort when releasing the connection.

BRIEF SUMMARY OF THE INVENTION

A percutaneous connector according to one aspect of the disclosure preferably includes a base having a base surface; one or more base magnets within the base defining a plurality of magnetic poles adjacent the base surface; a mating connector or cap having a cap surface; one or more cap magnets within the cap defining a plurality of magnetic poles adjacent the cap surface; the base magnets and cap magnets attract and align the cap and base with the cap surface and the base surface confronting one another; and a release mechanism adapted to at least partially separate the cap from the base when the cap is rotated relative to the base and out of alignment with the base.

The percutaneous connector may also include a skirt extending from the base. In one embodiment, the base magnets and cap magnets can each have their respective polar axes extending perpendicularly to the base surface and cap surface. At least one of the one or more base magnets may define at least one north pole and at least one south pole adjacent the base surface and at least one of the one or more cap magnets can define at least one north pole and at least one south pole adjacent to the cap surface. Further, at least one of the base magnets can have a polarity adjacent to the base surface opposite to the polarity of the other base magnets and at least one of the cap magnets can have a polarity adjacent to the cap surface opposite to the polarity of the other cap magnets. The plurality of poles defined by the base magnets and the cap magnets may be equally spaced such that each base magnet pole aligns with a cap magnet pole. The base and cap can have an unequal number of magnets to allow different orientations of the cap with respect to the base.

One aspect of the percutaneous connector according to the disclosure may allow rotation of the cap with respect to the base to misalign the cap and base magnets to reduce the magnetic attraction between the cap and base. Further rotation of the cap with respect to the base can cause magnetic repulsion between the cap magnets and base magnets. Such rotation may make release of the cap from the base easier for the patient, thereby reducing patient discomfort during release.

The release mechanism may include at least one cam formed at an oblique angle to the surface of one of the cap and base and at least one mating structure adapted to engage the at least one cam formed on the other of the cap and base.

The skirt extending from the base may comprise a flexible material and may have anchors associated with it. In at least one embodiment, the base is adapted to be implanted in a patient's skin and at least a portion of the base, positioned adjacent the patient's skin, can have a textured surface to promote skin ingrowth. In certain embodiments, this feature can help to reduce trauma and to provide lateral stabilization of the percutaneous connector.

The percutaneous connector may have a base contact connectable to a cap contact. In some embodiments, the base magnets and cap magnets are exposed at the base surface and cap surface. The percutaneous connector may include a channel extending through the base about which the base magnets are position and may also include a bore extending through the cap about which the cap magnets are positioned.

In another embodiment, the base contact and a cap contact can be configured to form an electrical connection providing two-way communication between an internal device and external controller.

The base contact and cap contact can each include at least one of a pin and socket. The internal device can include a ventricular assist device, or other subcutaneously implanted device that may need power, telemetry, command, or control.

The magnetic poles of the base magnets and cap magnets may extend perpendicularly to the base surface and cap surface; at least one of the base magnets can have a polarity adjacent the base surface opposite to the polarity of the other base magnets; and at least one of the cap magnets can have a polarity adjacent the cap surface opposite to the polarity of other cap magnets. One aspect of the disclosure describes that cap and base self-assembling when placed in close proximity to each other.

Another aspect of the disclosure includes a method of disconnecting a percutaneous connector establishing an electrical connection between an internal device and an external controller; the percutaneous connector including a cap and a base, the cap and base each having a plurality of magnets to attract the cap to the base and orient the cap on the base to establish an electrical connection; the method including rotating the cap relative to the base such that a cam positioned on one of the cap or base engages an element on the other of the cap or base, wherein the engaged cam and element cause relative separation between the cap and base; and pulling the cap away from the base.

BRIEF DESCRIPTION OF THE DRAWINGS

A more complete appreciation of the subject matter of the present invention and the various advantages thereof can be realized by reference to the following detailed description, in which reference is made to the accompanying drawings:

FIGS. 9A and 9B illustrate a sectional view of one embodiment of a pin of the present invention.

FIG. 10 illustrates one embodiment of an inert cap of the present invention.

DETAILED DESCRIPTION

In a first embodiment, illustrated in FIGS. 1-7, a percutaneous connector 1 comprises a cap 2 and a base 3. As will be discussed more fully below, the percutaneous connector 1 is designed to provide a detachable electrical connection between an internally implanted device and an external controller or device. One type of internal device contemplated for use with the percutaneous connector is disclosed in U.S. Pat. No. 6,688,861, the entirety of which is incorporated by reference as if fully set forth herein. The external controller used with the percutaneous connector may be similar to that disclosed in pending U.S. application Ser. No. 12/602,914 filed May 24, 2010, the entirety of which is incorporated by reference herein as if fully set forth herein. Other internal devices (e.g. a transcutaneous energy transfer (TET) system, pacemaker, insulin pump, dialysis device, automatic implantable cardioverter defibrillator) and external controllers, and associated power sources, may also be used with the percutaneous connector of the present invention.

Figure 1:
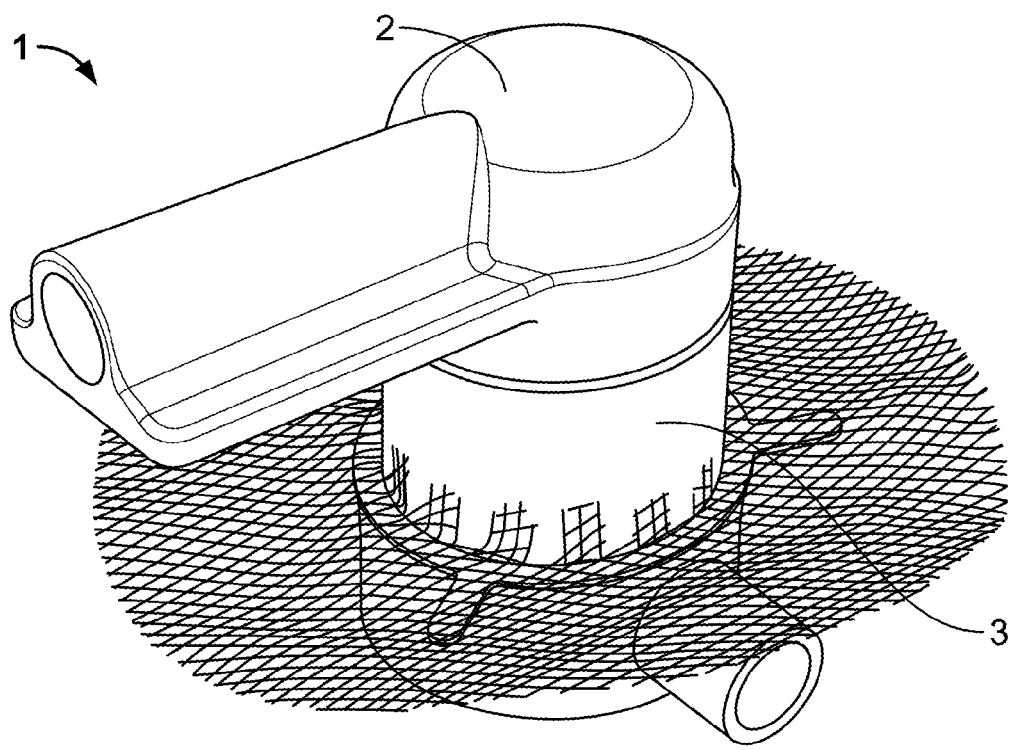
FIG. 1 illustrates one embodiment of the percutaneous connector of the present invention.

In the embodiment shown in FIG. 1, the cap 2 and base 3 are depicted having similar cross sectional diameters. In other embodiments, one of the cap and base could have a larger diameter than the other to form inter-fitting cylinders.

Figure 2:
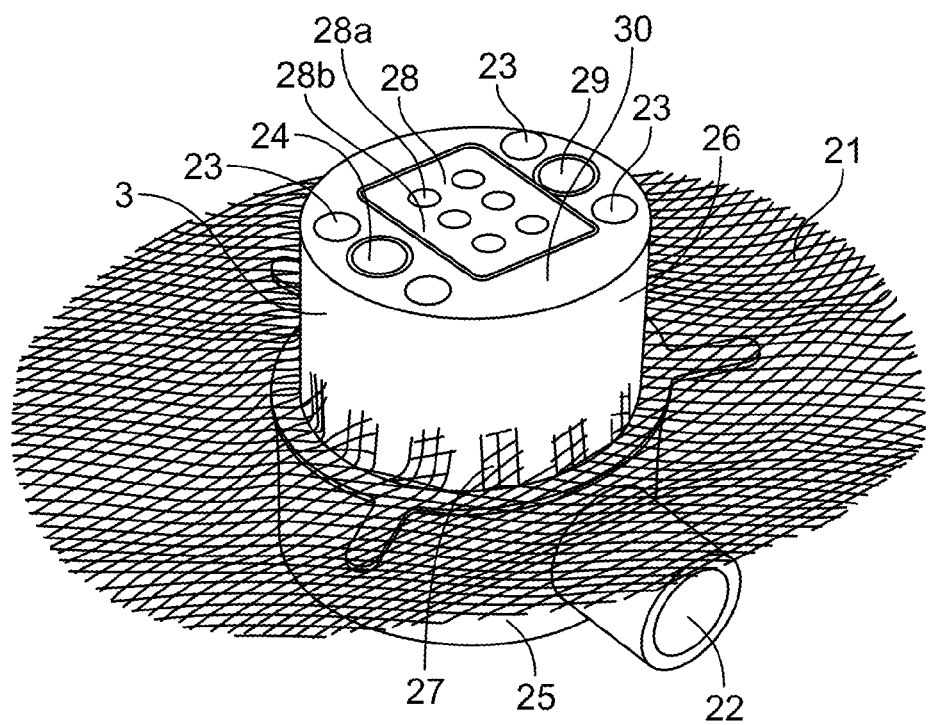
FIG. 2 illustrates a perspective view of the base of FIG. 1.

FIG. 2 details one embodiment of the base 3. The base 3 has an internal portion 25 and an external portion 26. The internal portion 25 is positioned in or under a patient's skin when the base 3 is implanted. The external portion 26 protrudes through the skin of the patient to provide a base surface 30 to connect to the cap, as will be discussed more fully below. The base 3 is preferably formed of titanium or other material suitable to be implanted into the body of a patient, though other biocompatible materials are also envisioned.

In the embodiment shown, the base 3 has an internal portion 25 adapted for mounting within the patient's body and an external portion 26 adapted for mounting at or near the skin so that a base surface 30 is exposed to the outside of the patient's body. A lateral stabilizer or skirt 21 extends radially from the base 3 and as illustrated, is positioned between the internal portion 25 and the external portion 26. The skirt 21 provides a surface for tissue ingrowth to prevent dislodgement of the base 3. It is believed that the skirt may also provide consistent orientation of the internal portion should the patient's weight or body shape change. Although the skirt is shown as a circular disk, other embodiments are also envisioned such as multiple extending strips, a square sheet, oval shaped, differing diameter or size and differing thickness, etc. The skirt 21 could also have anchors (e.g. barbs or other attaching features) associated with it to increase the anti-rotation power of the skirt. The skirt shown is a flexible mesh but could also be a perforated material such as titanium wool, titanium mesh or the like and could also be a polymer or other biocompatible material. The perimeter of the skirt is featured to minimize trauma or irritation to the muscle, fat, and/or skin layers as a result of repetitive movement.

The perforated or porous material of the skirt allows the ingrowth of tissue to intertwine with the skirt which may create an anchor with a footprint matching the geometric shape of the skirt. Therefore, a larger skirt will typically result in a greater anchoring force. A larger skirt may also result in spreading mechanical forces applied to the base over a larger region of the patient's skin. This decreases concentration of pressure on the skin in the immediate proximity of the base 3, and instead spread the pressure over the area of the skirt. The diffusion of pressure across the area of the skirt may reduce patient discomfort in situations where the cap and base experience contact with external elements, such as during removal of the cap. The skirt 21 can also have reinforcing members 33 to secure the skirt 21 to the base 3. The skirt could also include a silicon or Teflon ring extending around its perimeter, a Dacron or other woven fabric material design, or a rounder outer edge to minimize trauma around the perimeter of the skirt.

It is believed that a textured surface 27 around the base 3 further promotes skin ingrowth in the area just below where the base protrudes from the skin. The textured surface 27 can include the same material as that used for the skirt 21. Alternatively, the textured surface 27 could also incorporate other methods for providing a skin ingrowth area, for example, sintered titanium or other type of porous surface or patterned texturing surface application. Skin ingrowth around the exit site can provide a better seal to reduce the likelihood of infections resulting from internal exposure to external contaminants.

The skirt 21 can be positioned anywhere on the base 3 as desired. For example, if a more "low-profile" base 3 is desired, the skirt could instead be positioned higher on the base, such as adjacent to the base surface 30, so that the skirt will be disposed closer to the skin surface when the base is positioned in the patient's body. In this arrangement, most of the base would then be positioned under the patient's skin. In another alternative, more than one skirt can be included on the base to, for example, contact with multiple tissue layers in the epidermis. Such an alternative arrangement could also result in a more "low-profile" base and also improve the attachment of the base of the patient's skin.

Continuing with this embodiment, the base surface 30 has a set of base contacts 28. In this embodiment, the base contacts are in the form of metallic elements 28a, each defining a small recess. The metallic elements are disposed in a block 28b of dielectric material which insulates the contacts from one another. The base contacts 28 can be any type of connection that provides a detachable electrical connection. Merely by way of example, each metallic element may be a receptacle manufactured by Mill-Max Manufacturing Corp. of Oyster Bay, N.Y. for use with a mating element referred to as a "pogo pin" from the same manufacturer. As shown, the base 3 has magnets 24, 29 exposed at the base surface 30. The magnets 24, 29 each have their respective magnetic poles extending generally perpendicularly to the base surface 30, and thus also extending perpendicular to the patient's skin. The magnets 24, 29 can have opposite polarity exposed at the base surface 30. For example, magnet 24 could have its north pole exposed at the base surface 30 while magnet 29 has its south pole exposed, or vice versa. Magnets with opposite polarity exposed will assist a user in properly aligning the cap on the base during use. Although the base surface 30 is shown with two magnets, any number of magnets could be used. When more than two magnets are implemented, it is preferable that only one magnet has exposed polarity opposite that of the others for alignment purposes, although more than one could be arranged in this manner. In other embodiments, the base magnets can all have the same pole exposed. The magnets need not be exposed at the surface and instead could be positioned adjacent the surface.

The base surface 30 also has a release mechanism, depicted in this embodiment as multiple recesses 23. The recesses shown have a hemispherical shape. Thus, the outer portions of the recesses, close to the base surface 30 extend at an oblique angle to the base surface. The recesses could also be elliptical, angled, trapezoidal, etc. The recesses 23 can be implemented in cooperation with the cam members 45 (FIG. 4) of the cap 2 to properly align the cap 2 and base 3. The recess and cam members could be formed on either of the cap and base, or any combination thereof.

Figure 3:
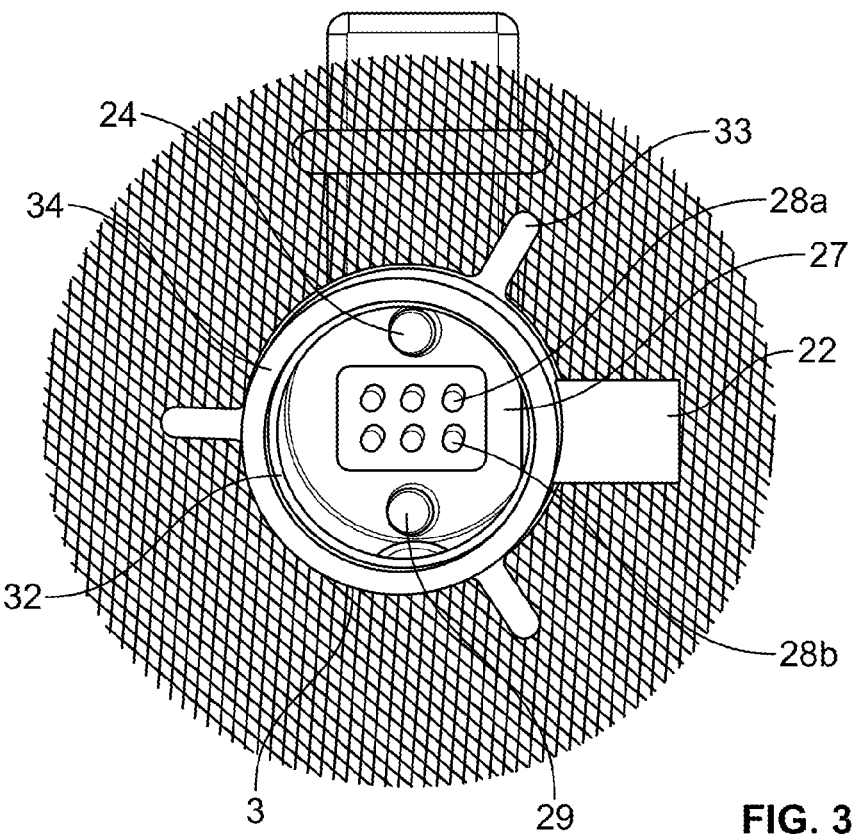
FIG. 3 illustrates a top view of the base of FIG. 2.
Figure 4:
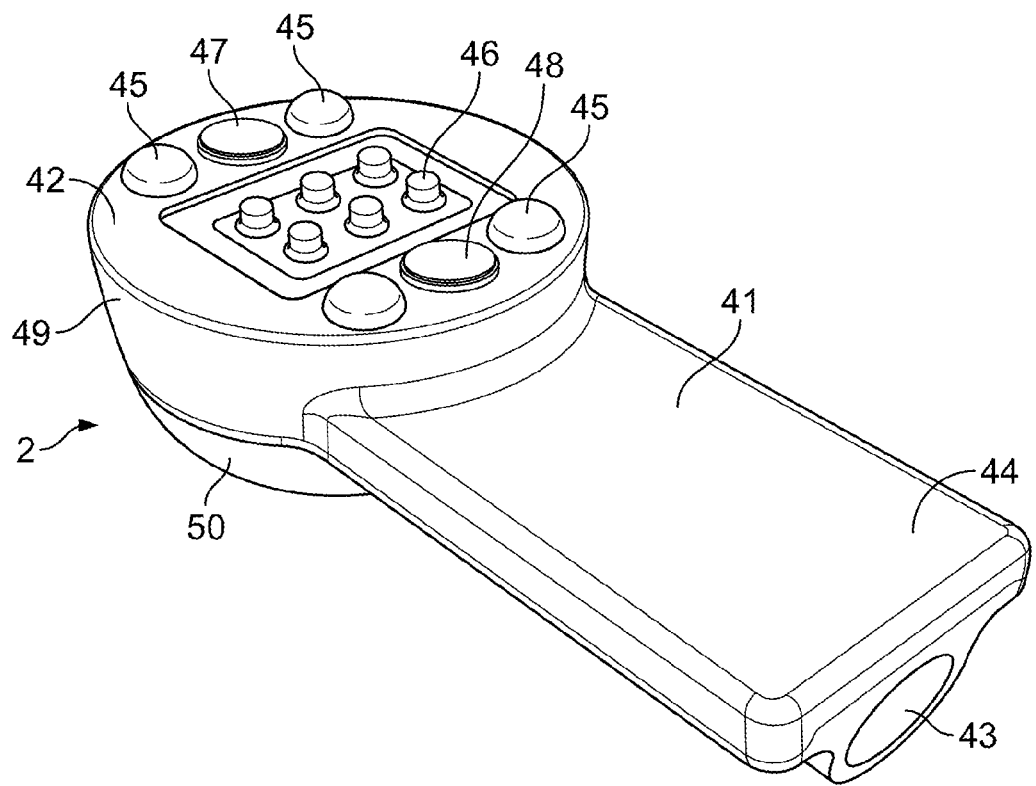
FIG. 4 illustrates a perspective view of a first portion of the cap of FIG. 1.
Figure 8:
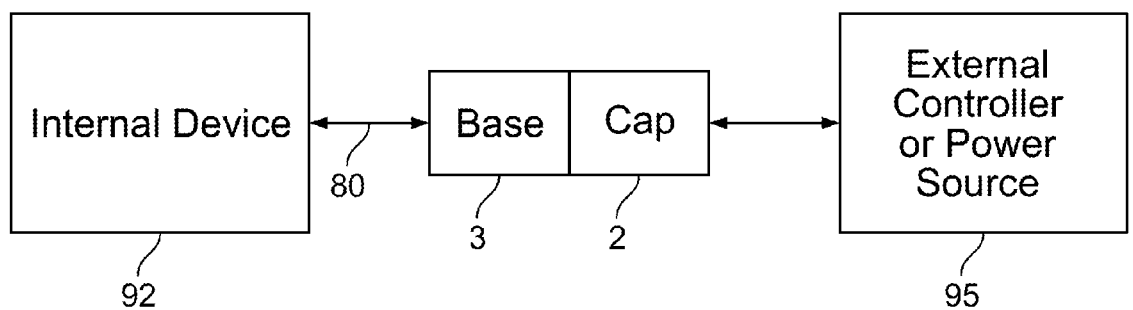
FIG. 8 illustrates a schematic drawing of a communication between an internal device and external controller.

FIG. 3 illustrates a bottom view of the base 3 showing the inner end 34, i.e., the end internal portion 25 which faces into the patient's body, and away from the skin surface, when the base 3 is implanted in the patient. Inner end 34 faces opposite from base surface 30 depicted in FIG. 2, with some elements removed for clarity of illustration. A channel 31 extends through the base 3 from the internal portion 25 toward the external portion 26 (FIG. 2). In the embodiment shown, a wall 37 (FIG. 3) blocks one end of the channel 31. The insulating block 28b and metallic contacts 28a are also shown. A conduit 22 extends from a side of the base 3 between wall 37 and inner end 34. Conduit 22 communicates with channel 31. The channel 31 and conduit 22 provide a passageway for an electrical conductor such as a multi-conductor cable 80 (FIG. 8) to connect with the contacts 28a. The electrical conductor or cable (not shown in FIG. 2) may pass out of the connector through the conduit, and may extend under the skin of a patient and within the patient's body to the internal device. The inner end 34, positioned on the opposite end of the channel from the base surface 30, has a ledge 32 to receive a plug (not shown) to effectively seal the channel 31. The plug can be attached to the base 3 prior to implanting to ensure no foreign materials enter the base. A detachable plug allows the installer to visually confirm that a proper connection has been established between the electrical connector and the base contact 28 prior to implanting. Alternatively, the base 3 could be manufactured with a permanent plug thereon. The plug and base are hermetically sealed to each other once they are coupled to together. Alternatively or additionally, the channel 31 may be filled with a dielectric potting material after connecting the conductor to the contacts 28b.

FIGS. 4-7 illustrate one embodiment of the cap 2 of the percutaneous connector of FIG. 1. The cap 2 in the embodiment shown has a first portion 41 (also shown in FIG. 5) and a second portion 50 (also shown in FIGS. 6-7). The first portion 41 has magnets 47, 48 exposed at a cap surface 42. The magnets 47, 48 are arranged in a pattern similar to that of the base magnets 24, 29 such that the base and cap magnets align when the cap surface and base surface are connected. Similarly to the base magnets, the cap magnets 47, 48 can have their magnetic pole axes extending perpendicularly to the cap surface 42. The cap magnets 47, 48 can have opposite magnetic poles exposed at the cap surface 42, similar to the base magnets 24, 29, as discussed above. In the embodiments where one of the magnetic poles is opposite, the result of such opposite polarity is that the cap 2 can only be coupled to the base 3 in a particular orientation. The magnets can also provide the additional benefit that as the cap and base are brought into proximity with each other, the magnets automatically align and couple the cap surface to the base surface.

In other embodiments, the cap and base can have an unequal number of magnets to allow the cap to be coupled to the base in more than one orientation. The base and cap could also have different sized magnets. The cap is preferably formed of a polymer such as HDPE or similar material, although other materials are also possible.

In other embodiments, the size of the cap can be smaller or larger relative to the base. A larger cap relative to the base can house larger magnets and therefore provide a stronger coupling force between the cap and base. A smaller cap relative to the base could provide a smaller coupling force.

As shown, the cap 2 has cam members 45 protruding from the cap surface. The cam members 45 are arranged to match the pattern of the recesses 23 on the base 3. The cam members 45 extend into the recess 23 when the cap 2 and base 3 are connected. In other embodiments, both cam members 45 and recesses 23 can be formed on the cap surface 42 and the base surface 30. Cam members 45 are generally hemispherical. Near the juncture of the cam members with the cap surface, the surface of each cam member is disposed at an oblique angle to the cap surface.

A set of cap contacts 46 is disposed in the cap. Cap contacts 46 project from cap surface 42. The cap contacts 46 mate with the base contact 28 to provide an electrical connection between an internal device and external controller. In this embodiment, each cap contact 46 is a spring force adjusted pin, commonly referred to as a "pogo pin". As shown in FIGS. 9A and 9B, each pogo pin includes a fixed body 91 and a mobile element 93 capable of limited translational movement along the pin axis. FIG. 9A shows the pogo pin with the mobile element 93 in the extended state. FIG. 9B shows the pogo pin in a compressed state. A spring 94 biases the mobile element to the extended state depicted in FIG. 9A. When the mobile element is in the extended state, it projects out of the cap surface 42. Each mobile element 93 can be moved toward a retracted state shown in FIG. 9B) and thus moved toward the cap surface. The use of contacts with mobile elements reduces the precision necessary in manufacturing the cam and recesses of the base and cap while still providing a secure electrical connection between the pin and receiver.

Another advantage of using contacts with mobile elements such as the pogo pins discussed above is that they maintain contact between the cap contacts and the base contacts as the cap is moved relative to the base. As the movement occurs, the mobile cap contacts wipe the surfaces of the base contacts. This wipe removes any oxide or contaminant from the electrical contact surfaces and counteracts electrical resistance build-up. Of course, other contact types could also be used to achieve this feature.

The cap 2 has an arm 44 extending from a head 49. The arm 44 preferably has an opening 43 extending through it to house an electrical connector (e.g. a wire) which connects the cap contact 46 to the external controller and/or power source.

Figure 5:
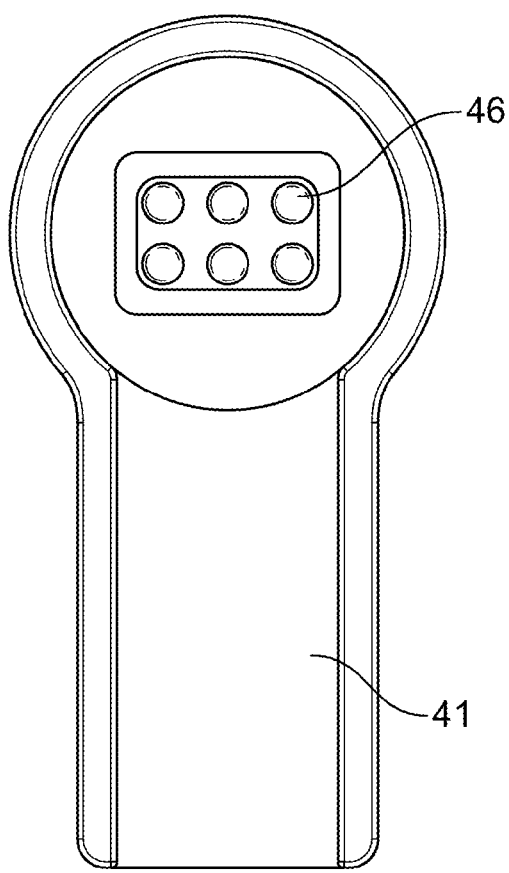
FIG. 5 illustrates a bottom view of the first portion of the cap of FIG. 4.

FIG. 5 shows a bottom view of the first portion 41 of the cap 2 of FIG. 1. The cap contact 46 extends through the first portion 41 of the cap 2. In the embodiment shown, the bottom of the first portion 41 is coupled to the top of the second portion 50 when the cap 2 is assembled.

Figure 6:
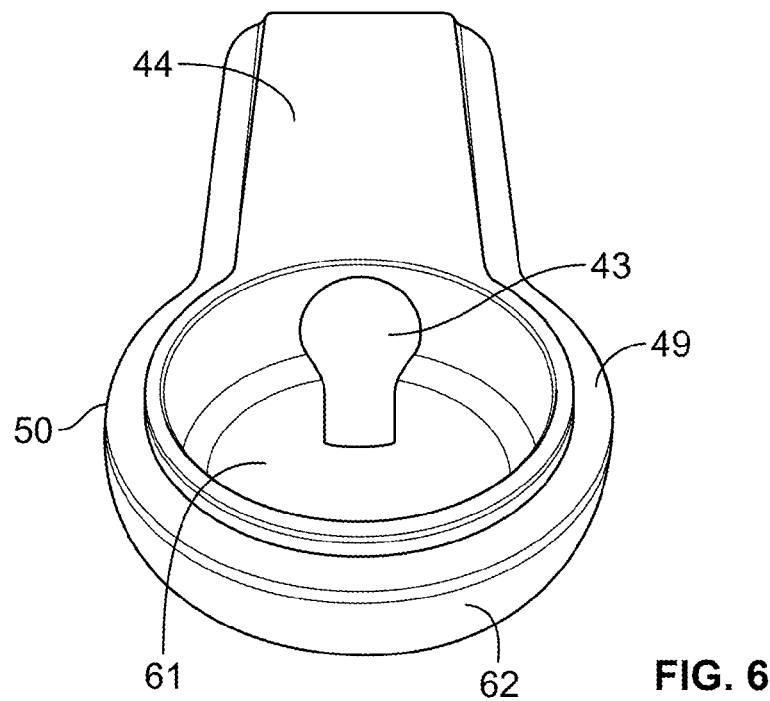
FIG. 6 illustrates a bottom view of the second portion of the cap of FIG. 1.
Figure 7:
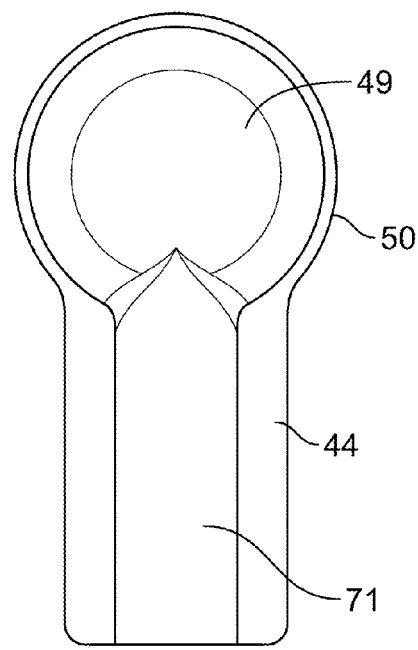
FIG. 7 illustrates a top view of the second portion of the cap of FIG. 1.

FIGS. 6 and 7 illustrate bottom and top views, respectively, of one embodiment of the second portion 50 of the cap 2 of FIG. 1. The second portion can have a bore 61 in the head 49 to receive a printed circuit board or other type of connection between an electrical conductor such as a multiconductor cable (not shown) and the cap contacts 46. Alternatively, the electrical conductor could also connect directly to the cap contacts 46. The bore 61 is in communication with the opening 43 to house the electrical connector. The second portion 50 has a ledge 62 extending around its perimeter to secure the first portion 41 thereto. As shown in FIG. 7, the top side 71 of the arm 44 extending from the head 49 is adapted to house an electrical conductor having a circular cross-section. However, the arm 44 can be adapted to house any shape electrical connector including square or flat connectors.

An electrical connection between an internal device and external controller is established when the cap contact 46 and base contact 28 are connected. The electrical connection provides one-way or two-way communication between the internal device and external controller as shown schematically in FIG. 8. For example, the external controller can provide power as well as operating signals to the internal device, while in two-way communication, the internal device can also provide operational feedback to the controller.

A user can engage the cap 2 and base 3 simply by bringing the cap and base close to one another, with the cap surface 42 facing generally toward the base surface 30. The magnetic poles of the cap and base cooperatively pull the cap and base toward one another, so that the cap surface is disposed adjacent the base surface and confronts the base surface. The magnetic poles also act to rotate the cap relative to the base about an axis perpendicular to the confronting cap and base surfaces until the cap is in the correct rotational position. In this correct position, each correct cap contact 46 is aligned with the correct base contact 28a. Also, in this correct position, the cam members 45 on the cap are aligned with the recesses 23 in the base surfaces. Notably, if the user attempts to assemble the cap and base with the cap 180 degrees out of the correct position, the magnetic poles of the cap and base will repel, rather than attract one another, and thus the cap cannot be assembled to the base.

The user may separate the cap 2 from the base 3 as necessary. In one embodiment, the present invention includes a method of separating the cap from the base including rotating the cap 2 relative to the base 3. As the cap 2 rotates, the oblique surfaces of the cam members 45 and recesses 23 will interact with one another to lift the cap away from the base, thereby causing relative separation between the cap 2 and base 3. The cap magnets 47, 48 and base magnets 24, 29 become misaligned as the cap rotates, and further, the distance between the cap and base magnets increases, thereby decreasing the magnetic attraction between the cap 2 and base 3. After the cam member 45 causes this relative separation between the two sets of magnets, the user can pull the cap away from the base.

The percutaneous connector may also include an inert cap 100 as shown in FIG. 10. The inert cap 100 has a head 102 similar to the head 49 of the cap 2. However, the inert cap 100 does not provide an electrical connection. Instead, the inert cap can be used to provide a seal when the inert cap is coupled to the base. The inert cap 100 includes wings 104 which a user can contact to detach the inert cap from the base. The inert cap can include any of the attachment and detachment features discussed above which couple the cap 2 to the base 3. For example, the inert cap preferably has the same attachment feature as the cap 2 to allow cap 2 and inert cap 100 to be used interchangeably with the base 3. The inert cap may also have holes with screw threads aligned with threaded holes in the base to receive a screw to secure the inert cap to the base. The inert cap 100 can also include a sealing member 102 extending around its face which promotes a waterproof seal between the inert cap and base, for example, when taking a shower.

Further, in embodiments with cap magnets having alternating polarity exposed at the cap surface and corresponding base magnets having opposite polarity, further rotation of the cap relative to the base can cause cap and base magnets with the same polarity to become aligned, thereby causing magnetic repulsion between the cap and base.

The cam and recess configuration may reduce discomfort for a patient in situations where the cap, for example, becomes snagged in a user's clothes or contacts another surface which causes the cap to dislocate from the base. The preferred hemispherical shape of the cam enables separation whether the cap is rotated, pushed, or otherwise moved with respect to the base.

The various embodiments of opposing magnets and release mechanism, such as the cam and recess configuration, may provide for reduced overall discomfort of the patient. This is particularly true in instances where the cap needs to be removed from the base. The release mechanism and/or opposing magnets allow for simplified release of the cap due to the reduced magnetic attraction between the cap and base. Further, the ability of the patient, or other individual, to manipulate the cap to decrease the magnetic attraction may also allow for the use of stronger magnets. As such, the stronger magnets may allow for an increased attraction between the cap and base, and thus fewer instances of accidental separation of the cap from the base.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A percutaneous connector comprising:
   a base having a base surface, at least a portion of the base having a textured surface to promote tissue ingrowth;
   a skirt extending from the base, the skirt including at least one from the group consisting of silicon and Polytetrafluoroethylene ring extending around its perimeter;
   one or more base magnets within the base defining a plurality of magnetic poles adjacent the base surface;
   a cap having a cap surface;
   one or more cap magnets within the cap defining a plurality of magnetic poles adjacent the cap surface, the base magnets and cap magnets attract the cap to the base and align the cap and base with the cap surface and base surface confronting one another; and
   a release mechanism adapted to at least partially separate the cap from the base when the cap is rotated relative to the base about an axis normal to the cap surface and base surface.

2. The percutaneous connector of claim 1, wherein the base magnets and the cap magnets each have their respective magnetic polar axes extending perpendicularly to the base surface and cap surface.

3. The percutaneous connector of claim 2, wherein at least one of the one or more base magnets define at least one north pole and at least one south pole adjacent to the base surface, and;
   wherein the one or more cap magnets define at least one north pole adjacent to the cap surface and at least one south pole adjacent to the cap surface.

4. The percutaneous connector of claim 3, wherein the base and cap have an unequal number of magnets to allow different orientations of the cap with respect to the base.

5. The percutaneous connector of claim 3, wherein the plurality of poles defined by the base magnets and the plurality of poles defined by the cap magnets are equally spaced such that each base magnet pole aligns with a cap magnet pole.

6. The percutaneous connector of claim 5, wherein rotation of the cap misaligns the base magnets and cap magnets to reduce the magnetic attraction between the cap and base.

7. The percutaneous connector of claim 6, wherein further rotation of the cap causes magnetic repulsion between the base magnets and the cap magnets.

8. The percutaneous connector of claim 1, wherein the release mechanism comprises at least one cam formed at an oblique angle to the surface of one of the cap and base and at least one mating structure adapted to engage the at least one cam formed on the other of the cap and base.

9. The percutaneous connector of claim 1, wherein the skirt comprises a flexible material.

10. The percutaneous connector of claim 9, wherein the textured surface includes the same material as that used for the skirt.

11. The percutaneous connector of claim 1, further comprising a plurality of anchors associated with the skirt.

12. The percutaneous connector of claim 1, wherein the base is adapted to be implanted at least partially in a patient's skin.

13. The percutaneous connector of claim 1, further comprising a base contact configured to be coupled to a cap contact.

14. The percutaneous connector of claim 1, wherein the base magnets and cap magnets are exposed at the base surface and cap surface.

15. The percutaneous connector of claim 1, further comprising a channel extending through the base, wherein the base magnets are positioned around the channel; and
   a bore extending through the cap, wherein the cap magnets are positioned around the bore.

16. The percutaneous connector of claim 1 wherein the base contact and cap contact are configured to form an electrical connection providing two-way communication between an internal device and external controller.

17. The percutaneous connector of claim 16, wherein the base contact and cap contact each comprise at least one of a pin and socket.

18. The percutaneous connector of claim 16, wherein the internal device comprises at least one of a ventricular assist device, insulin pump, pacemaker, automatic implantable cardioverter defibrillator, and dialysis device.

19. The percutaneous connector of claim 16, wherein the magnetic poles of the base magnets and cap magnets extend perpendicularly to the base surface and cap surface,
   at least one of the base magnets has a polarity adjacent the base surface opposite to the polarity of the other base magnets, and
   at least one of the cap magnets has a polarity adjacent the cap surface opposite to the polarity of the other cap magnets.

20. The percutaneous connector of claim 19, wherein the base and cap self-assemble when placed in close proximity to each other.

21. The percutaneous connector of claim 1, further comprising an inert cap adapted to be coupled to the base.

22. The percutaneous connector of claim 21, wherein the inert cap has one or more inert cap magnets within the inert cap defining a plurality of magnetic poles adjacent the inert cap surface.

23. The percutaneous connector of claim 22, wherein the inert cap has a sealing member creating a waterproof seal between the inert cap and the base.

24. A method of disconnecting a percutaneous connector establishing an electrical connection between an internal device and an external controller, the percutaneous connector including a cap, a base, and a skirt extending from the base, the skirt including at least one from the group consisting of silicon and Polytetrafluoroethylene ring extending around its perimeter, the cap and base each having a plurality of magnets to attract the cap to the base and orient the cap on the base to establish the electrical connection, the base having a base surface, at least a portion of the base having a textured surface to promote tissue ingrowth, the method comprising the steps of:
   rotating the cap relative to the base such that a cam positioned on one of the cap or base engages an element positioned on the other of the cap or base, wherein the engaged cam and element cause relative separation between the cap and base; and
   pulling the cap away from the base.

25. A percutaneous connector comprising:
   a base having a base surface, at least a portion of the base having a textured surface to promote tissue ingrowth;
   a skirt extending from the base, the skirt including at least one from the group consisting of silicon and Polytetrafluoroethylene ring extending around its perimeter;
   one or more base magnets within the base defining a plurality of magnetic poles adjacent the base surface;
   a cap having a cap surface; and one or more cap magnets within the cap defining a plurality of magnetic poles adjacent the cap surface, the base magnets and cap magnets attract the cap to the base and align the cap and base with the cap surface and base surface confronting one another.

* * * * *